United States Patent [19]

Leeper et al.

[11] Patent Number: 4,938,751

[45] Date of Patent: Jul. 3, 1990

[54] ELASTOMERIC BLADDERS FOR MEDICAL INFUSERS

[75] Inventors: Harold M. Leeper, Mountain View; George V. Guittard, Cupertino, both of Calif.

[73] Assignee: ALZA Corporation, Palo Alto, Calif.

[21] Appl. No.: 222,448

[22] Filed: Jul. 21, 1988

Related U.S. Application Data

[63] Continuation of Ser. No. 50,130, May 14, 1987, abandoned, which is a continuation of Ser. No. 237,325, Feb. 23, 1981, abandoned.

[51] Int. Cl.$^5$ ............................................. A61M 37/00
[52] U.S. Cl. ............................. 604/132; 128/DIG. 12
[58] Field of Search ............................. 604/132, 133; 128/DIG. 12

[56] References Cited

U.S. PATENT DOCUMENTS

| | | |
|---|---|---|
| 3,993,069 | 11/1976 | Buckles et al. ................ 128/214 |
| 4,140,117 | 2/1979 | Buckles et al. ................ 128/213 |
| 4,201,207 | 5/1980 | Buckles et al. ................ 128/214 |
| 4,386,929 | 6/1983 | Peery et al. .................... 604/132 |
| 4,419,096 | 12/1983 | Leeper et al. .................. 604/132 |

OTHER PUBLICATIONS

"Cab-O-Sil® Properties and Functions", Cabot Corporation, 1977, front and back covers, pp. 2, 11 and 30.
Materials and Compounding Ingredients for Rubber, Bill Communications, Inc. 1975, p. 122.
"'Ethyl' Antioxidant 330", Ethyl Corporation, front cover and p. 1.
The Vanderbilt Rubber Handbook, R. T. Vanderbilt Co., Inc. 1978, pp. 8-13.
Concise Encyclopedia of Chemical Technology, Wiley Interscience, pp. 1031-1036.

Primary Examiner—C. Fred Rosenbaum
Assistant Examiner—Sharon Rose
Attorney, Agent, or Firm—Steven F. Stone; Edward L. Mandell; Paul L. Sabatine

[57] ABSTRACT

Elastomeric bladders having improved resistance to spontaneous rupture when inflated are made by vulcanizing a homogeneous mixture of synthetic polyisoprene having 90% to 98% cis-1,4 linkages, 3 to 10 phr fumed silicon dioxide, and vulcanizing agent while simultaneously forming the mixture into hollow cylindrical bodies. After being formed the bodies are solvent extracted to remove unreacted vulcanizing agent and the degradation products of the vulcanizing agent. Following the solvent extraction about 0.2 to 2 phr of a nontoxic, nonleachable antioxidant are imbibed into the bodies by contacting the bodies with a liquid solution of the antioxidant.

47 Claims, No Drawings

ELASTOMERIC BLADDERS FOR MEDICAL INFUSERS

This application is a continuation of application Ser. No. 050,130, filed 5/14/87 which was a continuation of application Ser. No. 237,325, filed 2/23/81, both now abandoned.

TECHNICAL FIELD

The invention relates to synthetic polyisoprene bladders for medical infusers which have improved resistance to spontaneous rupture.

BACKGROUND ART

Medical devices that infuse liquids into patients are called infusers. One type of infuser uses an elastomeric bladder as its power source. Such infusers and bladders are described in U.S. Pat. Nos. 3,993,069 and 4,201,207. These infusers consist of a housing, an elastomeric bladder contained within the housing that is inflated with the liquid to be infused, and a conduit that leads from the bladder to the infusion site. The rate at which the liquid is infused from the infuser depends upon the pressure exerted on the liquid by the bladder, the viscosity of the liquid, and the flow restriction characteristics of the conduit. The above cited patents describe bladders that are capable of maintaining the pressure on the liquid substantially constant over discharge of a large proportion of the liquid. The bladders described in these patents are made from vulcanized synthetic polyisoprene that has a low frequency hysteresis less than about 10% and a stress relaxation less than about 10%. Such hysteresis and stress relaxation characteristics were considered as key factors in realizing substantially constant pressure performance.

In making large numbers of such bladders from synthetic polyisoprene it was found that a small but significant number of them ruptured when inflated—particularly after prolonged storage in an inflated state. Even though only a small portion of the bladders so ruptured it was desirable to decrease the incidence of rupture in order to provide a greater margin of safety against rupture in the marketplace. The above patents say nothing about reducing the incidence of bladder rupture.

A principal object of the present invention is to provide synthetic polyisoprene bladders that have a reduced incidence of rupture and acceptable pressure constancy performance.

DISCLOSURE OF THE INVENTION

One aspect of the invention is an elastomeric bladder for use in a medical infuser that has improved resistance to rupture when inflated, the bladder being a tubular body (a) made from a vulcanized homogeneous mixture of synthetic polyisoprene having about 90% to about 98% cis-1,4 linkages and particulate silicon dioxide or particulate carbon black which have a nominal average diameter in the range of about $1 \times 10^{-5}$ to about $5 \times 10^{-3}$ mm and (b) into which a nontoxic substantially nonleachable antioxidant has been diffused, the amounts of silicon dioxide or carbon black and antioxidant being sufficient to make the half-life of a population of the bladders at least about ten times longer than the half-life of a comparable population of bladders made from said vulcanized synthetic polyisoprene that do not include the silicon dioxide or carbon black and the antioxidant.

Another aspect of the invention is a process for making an elastomeric bladder for use in a medical infuser and having an improved resistance to rupture when inflated comprising:

(a) mixing homogeneously a synthetic polyisoprene having about 90% to about 98% cis-1,4 linkages, about 3 to about 10 phr particulate silicon dioxide or particulate carbon black which have a nominal average diameter in the range of about $1 \times 10^{-5}$ to about $5 \times 10^3$ mm, and an amount of vulcanizing agent sufficient to vulcanize the mixture;

(b) subjecting the mixture to vulcanizing conditions while simultaneously (c) forming the mixture into a tubular body;

(d) solvent extracting the degradation products of the vulcanizing agent from the body; and (e) diffusing about 0.2 to about 2 phr of a nontoxic substantially nonleachable antioxidant into the body by contacting the body with a liquid solution of the antioxidant.

As used herein the designation "phr" means parts per hundred parts of synthetic polyisoprene.

DETAILED DESCRIPTION OF THE INVENTION

The synthetic polyisoprene that is used to make the bladders has about 90% to about 98% of its monomeric units joined in cis-1,4 orientation. It is preferably of the type made using Ziegler catalysts which is characterized by having about 96% to about 98% cis-1,4 linkages. This polyisoprene is mixed homogeneously with particulate silicon dioxide or particulate carbon black or mixtures thereof which have the above indicated particle size. Fumed silicon dioxide is preferred. Such silicon dioxide is produced by the hydrolysis of silicon tetrachloride vapor in a flame of hydrogen and oxygen at temperatures above the fusion temperature of silica (ca 1710° C.). In this combustion process molten spheres of silica are formed that on cooling fuse with one another to form branched, three-dimensional, chain-like aggregates. The final product typically has a surface area in the range of about 150 to about 450 m²/gram as measured by the BET method. Such fumed silicon dioxides are sold by Cabot Corporation, Boston, Mass. under the trademark Cab-O-Sil®. The carbon black will typically have a surface area in the range of about 50 to about 250 m²/gram as measured by the BET method. The amount of silicon dioxide or carbon black that is mixed with the polyisoprene should be sufficient to substantially inhibit spontaneous rupture of the bladder due to the stresses that occur in the bladder walls when the bladder is inflated with medical fluid. About 3 to about 10 phr, preferably 3 to 7 phr, of the silicon dioxide or carbon black will normally be mixed with the synthetic polyisoprene. Lesser amounts will not give a significant increase in rupture resistance. More than 10 phr may be added, but such amounts do not produce correspondingly greater enhancement of rupture resistance and may affect the pressure constancy performance of the bladder adversely.

The polyisoprene-silicon dioxide/carbon black mixture is vulcanized to form carbon-to-carbon or monothio crosslinks at the 1 and 4 positions of the isoprene unit. To achieve such vulcanization a vulcanizing agent is added to the mixture and the mixture is subjected to vulcanization conditions. Vulcanizing agents and procedures that may be used are disclosed in U.S. Pat. No. 4,201,207 at column 2, line 54 to column 3, line 13 and in U.S. Pat. No. 3,993,069 at column 8, line 50 to column 10, line 35, which disclosures are incorporated herein by reference. Dicumyl peroxide added in amounts in the range of about 1 to 2 phr is a preferred vulcanizing agent. The vulcanization will typically be effected during the forming process that is used to make the tubular bodies from the mixture. One such process involves calendering the polyisoprene-silicon dioxide/-carbon black-vulcanizing agent mixture into a sheet and placing a disc-shaped segment of the sheet into a transfer mold that forms the sheet into hollow cylindrical tubes of the desired geometry. Conventional injection molding techniques may also be used to form the body. The molding temperature, pressure, and time are such as to achieve the desired vulcanization (crosslinking) of the polyisoprene. The geometry of the tubular bodies is the same as that disclosed in U.S. Pat. No. 3,993,069 at column 4, lines 26 to 41, which disclosure is incorporated herein by reference.

After the mixture is formed into tubular bodies, the bodies are extracted with a solvent that removes substantially all unreacted vulcanizing agent and the degradation products of the vulcanizing agent from the body. The solvent should have no lasting deleterious effects on the body and should not leave a toxic residue in or on the body. The particular solvent used and the extraction time and temperature will depend upon the vulcanizing agent that was used. The purpose of the extraction is to prevent contamination of the medical fluid that is ultimately charged to the bladder with the vulcanizing agent or its degradation products.

After the extraction, the antioxidant is imbibed into the bodies by placing them into contact with a solution of the antioxidant. The antioxidant enters the bodies, which are usually swollen several fold with solvent, by diffusion. The amount of anti-oxidant imbibed into a body will, accordingly, depend upon the diffusion coefficient of the body with respect to the antioxidant, the concentration of the antioxidant in the solution, the solubility of the antioxidant in the body, the thickness of the body, the equilibrium swelling volume that is characteristic of the elastomer-solvent combination, and the conditions (time and temperature) under which the contact is made. Preferably the same pure solvent is used for the extraction and the antioxidant imbibition. The amount of antioxidant imbibed into the body should be sufficient to inhibit oxidative degradation (and thus rupture) of the bladder, usually over a period of at least about one year. The quantity required to achieve such inhibition will depend on the particular antioxidant that is used. In the case of the hindered phenol antioxidants described below, about 0.2 to about 2 phr, preferably about 1 phr, will usually be imbibed. Antioxidants that are nontoxic, such as those approved and under the provisions of Title 21 of the Code of Federal Regulations for use in plastics that are used in association with drugs or food, and which are substantially nonleachable by the medical fluid with which the bladder is to be inflated may be used. The term "substantially nonleachable" means that the antioxidant is less than 0.1% by weight soluble in the medical fluid. Nontoxic hindered polyphenol antioxidants, such as tetrakis [methylene 3-(3',5'-di-t-butyl-4'-hydroxyphenyl) propionate] methane and 1,3,5-trimethyl-2,4,6-tris(3,5-di-t-butyl-4-hydroxybenzyl) benzene, are preferred antioxidants for use in the invention. After the desired amount of antioxidant has diffused into the body, the body is taken from the solution and the solvent is removed from the body, such as by drying at temperatures up to 50° C. At this stage, the bladder is ready for incorporation into the infuser.

The inclusion of the silicon dioxide or carbon black and the antioxidant in the bladder together substantially reduce the likelihood that the bladder will rupture spontaneously when it is inflated. This reduction (or increase in rupture resistance) may be quantified relative to synthetic polyisoprene bladders that do not contain silicon dioxide or carbon black and antioxidant by comparing the half-lives of populations of the respective bladders under the same inflation conditions. The half-life is the time period from inflation to rupture of 50% of the bladders in the population. A population of at least ten bladders is desired to ensure that the results are statistically significant. Such comparisons carried out at 40° C. indicate that the half-life of the invention bladders is at least 10 times, and typically more than 100 times, longer than the half-life of bladders that do not contain silicon dioxide or carbon black and antioxidant.

The following example illustrates one embodiment of the invention. This example is not intended to limit the invention and is offered only by way of exemplification.

Preparation of Mixture

One hundred parts of synthetic polyisoprene (Natsyn 2200, 96% to 98% cis-1,4 linkages) were added to a Farrell Laboratory Mill (6 in.×13 in. rolls) at 130±10° F. and the gap between rolls was adjusted to 0.08–0.09 in. After about 3 minutes of milling, 5.0 phr fumed silicon dioxide (Cab-O-Sil ® M5, 200±25 m²/gram surface area, $1.4 \times 10^{-5}$ mm nominal average diameter) were added to the mill over a 5 min. period. One and one-half phr of dicumyl peroxide (Di-Cup R) were then added to the polyisoprene-silicon dioxide mix in four equal portions. Milling was continued until at least 18 min. had elapsed from the time the polyisoprene was added to the mill.

Vulcanization and Molding

The above mixture was charged to a four-cavity transfer mold maintained at 325–330° F. and having 25,000 kg of clamping force. The mold cavities and mandrels were designed to make hollow cylindrical bladders 74.6 mm long with a 6.63 mm outer diameter and 5.16 mm inner diameter and having an integral circular flange at each end 1.587 mm wide and 12.7 mm in diameter. The curing time was 20 min.

Extraction

Bladders formed and vulcanized as above were placed vertically in the extraction pot of a Soxhlet extraction apparatus fitted to a 1000 ml flask. Enough ethyl acetate was added to fill the Soxhlet apparatus and have 250 ml of ethyl acetate in the flask. The flask was heated and extraction of the bladders with the ethyl acetate was carried out for four hours.

Imbibition of Antioxidant

A 1.1% by weight solution of 1,3,5-trimethyl-2,4,6-tris(3,4-di-t-butyl-4-hydroxybenzyl) benzene in ethyl acetate was placed in a flask. Freshly extracted bladders were placed into the solution and kept there at ambient temperature for four hours. Previous tests had shown that the relationship between the wt. % of this antioxidant imbibed into the bladders was linear with 0.45% imbibed at a 1% concentration, and 0.68% imbibed at 1.5% concentration (four hours imbibition time). Accordingly about 0.5 phr antioxidant was imbibed into the bladders.

Half-life Tests

Half-life tests were carried out on bladders prepared as above except that 1.2 phr of tetrakis [methylene 3-(3',5'-di-t-butyl-4'-hydroxyphenyl) propionate] methane was imbibed into the bladders from an acetone/toluene solution instead of the above described antioxidant. A population of 24 of these bladders inflated with 60 ml water and kept in air at 40° C. had a half-life of approximately 14 months. Similar tests on populations of synthetic polyisoprene bladders made in substantially the same manner but without silicon dioxide or antioxidant indicate such bladders have a half-life of about 1 to 2 days.

Modification of the above-described bladders that are obvious to those of ordinary skill in the arts related to the invention are intended to be within the scope of the following claims.

We claim:

1. An elastomeric bladder that is for use in a medical infuser and has improved resistance to rupture when inflated, the bladder being a tubular body:
   (a) made from a vulcanized homogeneous mixture of synthetic polyisoprene having about 90% to about 98% cis-1,4 linkages and a material selected from the group consisting of particulate silicon dioxide and particulate carbon black having a nominal average diameter in the range of about $1 \times 10^{-5}$ to about $5 \times 10^{-3}$ mm;
   (b) into which a nontoxic, substantially nonleachable antioxidant has been diffused after vulcanization; and
   (c) the amounts of silicon dioxide, carbon black and antioxidant being sufficient to make the inflated half-life of a population of the bladders at 40° C. at least about ten times longer than the half-life of a comparable population of bladders made from said vulcanized synthetic polyisoprene but without the silicon dioxide, carbon black and the antioxidant.

2. The bladder of claim 1 wherein the said particulate material is silicon dioxide.

3. The bladder of claim 1 wherein the synthetic polyisoprene has about 96% to 98% cis-1,4 linkages.

4. The bladder of claim 1 wherein the vulcanized synthetic polyisoprene is characterized by having carbon-to-carbon crosslinks.

5. The bladder of claim 1 wherein said antioxidant is a hindered polyphenol.

6. The bladder of claim 2 wherein said antioxidant is a hindered polyphenol.

7. The bladder of claim 1 wherein said antioxidant is a material selected from the group consisting of tetrakis [methylene 3-(3',5',di-t-butyl-4'hydroxyphenyl) propionate] methane and 1,3,5-trimethyl-2,4,6-tris (3,5-di-t-butyl-4-hydroxybenzyl) benzene.

8. The bladder of claim 2 wherein said antioxidant is a material selected from the group consisting of tetrakis [methylene 3-(3',5',di-t-butyl-4'hydroxyphenyl) propionate] methane and 1,3,5-trimethyl-2,4,6-tris (3,5-di-t-butyl-4-hydroxybenzyl) benzene.

9. An elastomeric bladder that is for use in a medical infuser and has improved resistance to rupture when inflated, the bladder being a tubular body:
   (a) made from a vulcanized homogeneous mixture of synthetic polyisoprene having about 90% to about 98% cis-1,4 linkages and from about 3 to about 10 phr of a material selected from the group consisting of particulate silicon dioxide and particulate carbon black having a nominal average diameter in the range of about $1 \times 10^{-5}$ to about $5 \times 10^{-3}$ mm;
   (b) into which from about 0.2 to about 2 phr of a nontoxic, substantially nonleachable antioxidant has been diffused after vulcanization; and
   (c) the inflated half-life of a population of said bladders at 40° C. being at least about ten times longer than the half-life of a comparable population of bladders made from said vulcanized synthetic polyisoprene but without the silicon dioxide, carbon black and antioxidant.

10. The bladder of claim 9 wherein the particulate material is silicon dioxide.

11. The bladder of claim 9 wherein the synthetic polyisoprene has about 96% to 98% cis-1,4 linkages.

12. The bladder of claim 1 wherein the vulcanized synthetic polyisoprene is characterized by having carbon-to-carbon crosslinks.

13. The bladder of claim 9 wherein said antioxidant is a hindered polyphenol.

14. The bladder of claim 10 wherein said antioxidant is a hindered polyphenol.

15. The bladder of claim 9 wherein said antioxidant is selected from the group consisting of tetrakis [methylene 3-(3',5',di-t-butyl-4'hydroxyphenyl) propionate] methane and 1,3,5-trimethyl-2,4,6-tris (3,5-di-t-butyl-4-hydroxybenzyl) benzene.

16. The bladder of claim 32 wherein said antioxidant is selected from the group consisting of tetrakis [methylene 3-(3',5',di-t-butyl-4'hydroxyphenyl) propionate] methane and 1,3,5-trimethyl-2,4,6-tris (3,5-di-t-butyl-4-hydroxybenzyl) benzene.

17. An elastomeric bladder that is for use in a medical infuser, the bladder being a tubular body:
   (a) made from a homogeneous vulcanized mixture of polyisoprene having about 90% to 98% cis-1,4 linkages and about 3 to about 10 phr fumed silicon dioxide; and
   (b) into which about 0.2 to about 2 phr of a nontoxic, substantially nonleachable antioxidant has been diffused after vulcanization;
   whereby said bladder will have an improved resistance to rupture when inflated at 40° C., as compared to bladders formed from said polyisoprene without said silicon dioxide and said antioxidant.

18. The bladder of claim 17 wherein the synthetic polyisoprene has about 96% to 98% cis-1,4 linkages and the vulcanized polyisoprene is characterized by having carbon-to-carbon crosslinks.

19. The bladder of claim 18 wherein said silicon dioxide is present in amounts of about 3 to about 7 phr and said silicon dioxide has a surface area in the range of about 150 to about 450 m$^2$/gram.

20. The bladder of claim 19 wherein the surface area is 200±20 m$^2$/gram.

21. The bladder of claim 17 wherein the antioxidant is a hindered polyphenol.

22. The bladder of claim 21 wherein the hindered polyphenol is tetrakis [methylene 3-(3',5',di-t-butyl-4'hydroxyphenyl) propionate] methane or 1,3,5-trimethyl-2,4,6-tris (3,5-di-t-butyl-4-hydroxybenzyl) benzene.

23. An elastomeric bladder that is for use in a medical infuser and has improved resistance to spontaneous rupture when inflated at 40° C., the bladder being a tubular body:
   (a) made from a homogeneous mixture of synthetic polyisoprene having about 96% to about 98% cis-1,4 linkages and about 5 phr fumed silicon dioxide having a surface area of 200±20 m²/gram, the mixture being vulcanized with about 1.5 phr dicumyl peroxide; and
   (b) into which about 1 phr of 1,3,5-trimethyl-2,4,6-tris (3,5-di-t-butyl-4-hydroxybenzyl) benzene has been diffused after vulcanization.

24. A process for making an elastomeric bladder for use in a medical infuser and having improved resistance to rupture when inflated comprising:
   (a) mixing homogeneously a synthetic polyisoprene having a molecular structure with about 90% to about 98% cis-1,4 linkages, a material selected from the group consisting of particulate silicon dioxide and particulate carbon black having a nominal average diameter in the range of about $1 \times 10^{-5}$ to about $5 \times 10^{-3}$ mm and an amount of vulcanizing agent sufficient to vulcanize the mixture;
   (b) subjecting the mixture to vulcanizing conditions while simultaneously forming the mixture into a tubular body;
   (c) solvent extracting unreacted vulcanizing agent and the degradation products of the vulcanizing agent from the body; and
   (d) diffusing an amount of a nontoxic, substantially nonleachable antioxidant into the body by contacting the body with a liquid solution of the antioxidant;
   the amount of particulate material together with the amount of antioxidant diffused into the body after vulcanization being sufficient to make the inflated half-life at 40° C. of a population of bladders so formed at least about ten times longer than a comparable population of bladders without the particulate material and the antioxidant.

25. The process of claim 24 wherein in step (a) said particulate material is silicon dioxide.

26. The process of claim 25 wherein the synthetic polyisoprene has about 96% to about 98% cis-1,4 linkages and the vulcanizing agent effects carbon-to-carbon crosslinks in the polyisoprene.

27. The process of claim 21 wherein the amount of silicon dioxide is about 3 to about 10 phr, the antioxidant is a hindered polyphenol, and the amount of antioxidant is about 0.5 to about 2 phr.

28. The process of claim 27 wherein the amount of silicon dioxide is about 3 to about 7 phr, the antioxidant is a hindered polyphenol, and the amount of antioxidant is about 0.5 to about 2 phr.

29. The process of claim 25 wherein the silicon dioxide has a surface area of 200±20 m²/gram, the amount of silicon dioxide is 5 phr, the amount of vulcanizing agent is 1.5 phr, the antioxidant is selected from the group consisting of tetrakis [methylene 3-(3′,5′,di-t-butyl-4′hydroxyphenyl) propionate] methane and 1,3,5-trimethyl-2,4,6-tris (3,5-di-t-butyl-4-hydroxybenzyl) benzene, and the amount of antioxidant is about 0.2 to about 2 phr.

30. The process of claim 29 wherein the antioxidant is 1,3,5-trimethyl-2,4,6-tris(3,5-di-t-butyl-4-hydroxybenzyl) benzene, the amount of antioxidant is 1 phr, the solvent is ethyl acetate, and the antioxidant is dissolved in ethyl acetate.

31. A process for making an elastomeric bladder having an improved resistance to rupture when inflated, said process comprising the steps of:
   (a) mixing homogeneously (i) a synthetic polyisoprene having a molecular structure with about 90% to about 98% cis-1,4 linkages, (ii) an amount of dicumyl peroxide sufficient to vulcanize the mixture, and (iii) from about 3 to about 10 phr of particulate silicon dioxide having a nominal average diameter in the range of about $1 \times 10^{-5}$ to about $5 \times 10^{-3}$ mm;
   (b) subjecting the mixture to vulcanizing conditions while simultaneously forming the mixture into a tubular body;
   (c) solvent extracting unreacted vulcanizing agent and the degradation products of the vulcanizing agent from the body with ethyl acetate;
   (d) diffusing from about 0.2 to about 2 phr of a nontoxic, substantially nonleachable hindered polyphenol antioxidant into the body by contacting the vulcanized body with an ethyl acetate solution of the antioxidant;
   whereby the inflated half-life at 40° C. of a population of bladders so formed is at least ten times greater than a comparable population of bladders formed without the silicon dioxide and antioxidant.

32. The process of claim 31 wherein the synthetic polyisoprene has about 96% to about 98% cis-1,4 linkages.

33. The process of claim 31 wherein the amount of silicon dioxide is about 3 to about 7 phr and the amount of antioxidant is about 0.5 to about 2 phr.

34. The process of claim 31 wherein the silicon dioxide has a surface area of 200 20 m²/gram, the amount of silicon dioxide is about 5 phr, the amount of vulcanizing agent is about 1.5 phr and the antioxidant is selected from the group consisting of tetrakis [methylene 3-(3′,5′,di-t-butyl-4′hydroxyphenyl) propionate] methane and 1,3,5-trimethyl-2,4,6-tris (3,5-di-t-butyl-4-hydroxybenzyl) benzene.

35. The process of claim 34 wherein the antioxidant is 1,3,5-trimethyl-2,4,6-tris (3,5-di-t-butyl-4-hydroxybenzyl) benzene and the amount of antioxidant is about 1 phr.

36. The bladder produced by the process of claim 24.
37. The bladder produced by the process of claim 25.
38. The bladder produced by the process of claim 26.
39. The bladder produced by the process of claim 27.
40. The bladder produced by the process of claim 28.
41. The bladder produced by the process of claim 29.
42. The bladder produced by the process of claim 30.
43. The bladder produced by the process of claim 31.
44. The bladder produced by the process of claim 32.
45. The bladder produced by the process of claim 33.
46. The bladder produced by the process of claim 34.
47. The bladder produced by the process of claim 35.

* * * * *